United States Patent
Sandor (10) Patent No.: US 9,918,501 B2
(45) Date of Patent: Mar. 20, 2018

(54) GOGGLE FACIAL CUSHION

(71) Applicant: Spy Optic Inc., Carlsbad, CA (US)

(72) Inventor: Brent Sandor, Encinitas, CA (US)

(73) Assignee: Spy Optic Inc., Carlsbad, CA (US)

( * ) Notice: Subject to any disclaimer, the term of this patent is extended or adjusted under 35 U.S.C. 154(b) by 249 days.

(21) Appl. No.: 14/808,308

(22) Filed: Jul. 24, 2015

(65) Prior Publication Data
US 2015/0327601 A1  Nov. 19, 2015

Related U.S. Application Data

(62) Division of application No. 13/233,740, filed on Sep. 15, 2011, now Pat. No. 9,138,026.

(51) Int. Cl.
| | | |
|---|---|---|
| *A41D 13/00* | (2006.01) | |
| *A42B 3/18* | (2006.01) | |
| *B32B 3/30* | (2006.01) | |
| *A61F 13/537* | (2006.01) | |
| *A41D 13/015* | (2006.01) | |
| *A61F 9/02* | (2006.01) | |
| *B63C 11/12* | (2006.01) | |
| *A41D 13/11* | (2006.01) | |
| *A63B 33/00* | (2006.01) | |

(52) U.S. Cl.
CPC .............. *A41D 13/00* (2013.01); *A42B 3/185* (2013.01); *A61F 9/026* (2013.01); *A41D 13/0158* (2013.01); *A41D 13/1176* (2013.01); *A61F 9/027* (2013.01); *A61F 13/537* (2013.01); *A63B 33/002* (2013.01); *B32B 3/30* (2013.01); *B63C 11/12* (2013.01)

(58) Field of Classification Search
CPC ..... A41D 13/00; A41D 13/1176; A61F 9/026; A61F 9/027; A63B 33/002; B63C 11/12; A42B 3/185
See application file for complete search history.

(56) References Cited

U.S. PATENT DOCUMENTS

| | | | |
|---|---|---|---|
| 540,746 A * | 6/1895 | Lamb | A61F 9/02 |
| | | | 2/439 |
| 1,963,437 A | 6/1934 | Gray | |
| D138,545 S | 8/1944 | Splaine | |

(Continued)

FOREIGN PATENT DOCUMENTS

| | | |
|---|---|---|
| CA | 2456476 | 3/2004 |
| DE | 2063092 | 7/1971 |

(Continued)

*Primary Examiner* — Donald J Loney
(74) *Attorney, Agent, or Firm* — Stetina Brunda Garred & Brucker (57) ABSTRACT

A facial cushion for a goggle may have a plurality of layers which provide cushioning, cooling and ergonomic fit functions. The top layer which contacts the wearer's face may have an embossed pattern which creates an air space between the wearer's face and the top layer for providing a cooling function. The embossed top layer also increases the total surface area of the top layer thereby increasing its wicking ability and reduces the total skin contact surface area of the top layer reducing heat. Additionally, the cushion may be thicker at left and right end portions to maintain contact with the wearer's face despite pulling of the left and right ends of the goggle when the goggle is worn with a helmet.

20 Claims, 5 Drawing Sheets

(56) References Cited

U.S. PATENT DOCUMENTS

| | | |
|---|---|---|
| D146,237 S | 1/1947 | Sills et al. |
| 2,526,737 A | 10/1950 | Farina |
| 2,612,639 A | 10/1951 | Christensen |
| 3,056,140 A | 10/1962 | Lindblom |
| 2,398,031 A | 1/1967 | Morgan |
| 3,363,262 A | 1/1968 | Lindblom |
| 3,377,626 A | 4/1968 | Smith |
| 3,395,406 A | 8/1968 | Smith |
| 3,505,680 A | 4/1970 | Ring |
| 3,533,686 A | 10/1970 | O'Shea |
| 3,754,298 A | 8/1973 | Menil |
| D228,583 S | 10/1973 | LeBlanc |
| 3,783,452 A | 1/1974 | Benson et al. |
| 3,825,953 A | 7/1974 | Hunter |
| 3,896,496 A | 7/1975 | Leblanc et al. |
| 3,924,271 A | 12/1975 | Hirschmann, Jr. |
| 3,931,646 A | 1/1976 | Loughner |
| 3,945,044 A | 3/1976 | McGee et al. |
| D242,666 S | 12/1976 | Smith |
| 4,011,595 A | 3/1977 | Shields |
| 4,149,276 A | 4/1979 | Castro |
| 4,150,443 A | 4/1979 | McNeilly |
| 4,176,410 A | 12/1979 | Matthias |
| 4,264,987 A | 5/1981 | Runckel |
| 4,290,673 A | 9/1981 | Yamamoto |
| 4,317,240 A | 3/1982 | Angerman et al. |
| 4,425,669 A | 1/1984 | Grendol et al. |
| 4,428,081 A | 1/1984 | Smith |
| 4,435,852 A | 3/1984 | Nesler |
| 4,443,893 A | 4/1984 | Yamamoto |
| 4,447,914 A | 5/1984 | Jannard |
| 4,455,689 A | 6/1984 | Boyer |
| 4,528,701 A | 7/1985 | Smith |
| 4,556,995 A | 12/1985 | Yamamoto |
| 4,571,748 A | 2/1986 | Carroll et al. |
| 4,603,442 A | 8/1986 | Barfied |
| 4,670,914 A | 6/1987 | Harris |
| 4,698,838 A | 9/1987 | Angermann |
| 4,707,863 A | 11/1987 | McNeal |
| 4,716,601 A | 1/1988 | McNeal |
| 4,852,189 A | 8/1989 | Duggan |
| 4,868,929 A | 9/1989 | Curcio |
| 4,918,753 A | 4/1990 | Mermillod |
| 4,977,627 A | 12/1990 | Metcalfe et al. |
| 4,989,274 A | 2/1991 | Patelski, III |
| 5,018,223 A | 5/1991 | Dawson et al. |
| 5,027,443 A | 7/1991 | Watkins |
| 5,056,163 A | 10/1991 | Chou |
| 5,069,541 A | 12/1991 | Holmes et al. |
| 5,093,940 A | 3/1992 | Nishiyama |
| 5,138,723 A | 8/1992 | Bolle |
| 5,148,550 A | 9/1992 | Hodgkinson et al. |
| 5,182,817 A | 2/1993 | Branum |
| D334,758 S | 4/1993 | Reymondet et al. |
| 5,213,241 A | 5/1993 | Dewar et al. |
| 5,216,759 A | 6/1993 | Hewitt et al. |
| 5,339,119 A | 8/1994 | Gardner |
| 5,341,516 A | 8/1994 | Keim |
| D351,850 S | 10/1994 | Bolle |
| 5,359,370 A | 10/1994 | Mugnier |
| 5,363,512 A | 11/1994 | Grabos, Jr. et al. |
| 5,371,555 A | 12/1994 | Nagel |
| D358,159 S | 5/1995 | Lai |
| 5,410,763 A | 5/1995 | Bolle |
| 5,421,037 A | 6/1995 | Schulze |
| 5,423,092 A | 6/1995 | Kawai |
| 5,452,480 A | 9/1995 | Ryden |
| 5,471,036 A | 11/1995 | Sperbeck |
| 5,495,623 A | 3/1996 | Leonardi |
| 5,511,251 A | 4/1996 | Brakas |
| 5,517,700 A | 5/1996 | Hoffman |
| 5,542,130 A | 8/1996 | Grabos et al. |
| 5,564,132 A | 10/1996 | Kuo |
| 5,617,588 A | 4/1997 | Canavan et al. |
| 5,628,072 A | 5/1997 | Haslbeck |
| 5,636,388 A | 6/1997 | Hodges |
| 5,642,530 A | 7/1997 | Parks |
| 5,650,866 A | 7/1997 | Haslbeck |
| 5,652,965 A | 8/1997 | Crooks |
| 5,655,228 A | 8/1997 | Chiang |
| 5,657,106 A | 8/1997 | Herald, Jr. et al. |
| 5,685,022 A | 11/1997 | Essman et al. |
| 5,687,428 A | 11/1997 | Yamamoto |
| 5,689,834 A | 11/1997 | Wilson |
| 5,711,035 A | 1/1998 | Haslbeck |
| D391,594 S | 3/1998 | Huh |
| 5,768,716 A | 6/1998 | Porsche |
| 5,802,622 A | 9/1998 | Baharad et al. |
| 5,809,580 A | 9/1998 | Arnette |
| 5,813,990 A | 9/1998 | Ryll |
| 5,815,235 A | 9/1998 | Runckel |
| 5,845,341 A | 12/1998 | Barthold et al. |
| D403,689 S | 1/1999 | Mage |
| D405,102 S | 2/1999 | Moritz et al. |
| 5,867,841 A | 2/1999 | Chiang |
| 5,915,542 A | 6/1999 | Swiet |
| 5,927,281 A | 7/1999 | Monteleone et al. |
| 5,937,439 A | 8/1999 | Barthold et al. |
| 5,940,891 A | 8/1999 | Lane |
| D413,915 S | 9/1999 | Newcomb et al. |
| 5,966,745 A | 10/1999 | Schwartz et al. |
| 5,966,746 A | 10/1999 | Reedy et al. |
| 6,009,564 A | 1/2000 | Tackles et al. |
| 6,038,706 A | 3/2000 | Seiler |
| 6,038,707 A | 3/2000 | Ryden et al. |
| 6,047,410 A | 4/2000 | Dondero |
| 6,049,917 A | 4/2000 | Ryden |
| 6,059,408 A | 5/2000 | Bonacci |
| 6,062,688 A | 5/2000 | Vinas |
| 6,067,664 A | 5/2000 | Cortes |
| 6,076,196 A | 6/2000 | Masumoto |
| D428,039 S | 7/2000 | Thixton |
| 6,092,243 A | 7/2000 | Wu et al. |
| 6,094,751 A | 8/2000 | Parks |
| 6,098,204 A | 8/2000 | Arnette |
| 6,098,205 A | 8/2000 | Schwartz et al. |
| 6,099,120 A | 8/2000 | De Lima |
| 6,105,177 A | 8/2000 | Paulson et al. |
| 6,119,276 A | 9/2000 | Newcomb et al. |
| 6,138,285 A | 10/2000 | Robrahn et al. |
| 6,138,286 A | 10/2000 | Robrahn et al. |
| D442,206 S | 5/2001 | Meyerhoffer |
| 6,227,665 B1 | 5/2001 | Pernicka et al. |
| 6,253,387 B1 | 7/2001 | Yu |
| 6,282,727 B1 | 9/2001 | Lindahl |
| 6,282,728 B1 | 9/2001 | Baragar et al. |
| 6,321,391 B1 | 11/2001 | Basso |
| 6,367,091 B1 | 4/2002 | Chiang |
| D457,545 S | 5/2002 | Khulusi |
| D457,551 S | 5/2002 | Khulusi |
| 6,415,452 B1 | 7/2002 | Watanabe et al. |
| 6,460,196 B2 | 10/2002 | Tsubooka et al. |
| 6,467,098 B1 | 10/2002 | Lee |
| 6,513,925 B1 | 2/2003 | Bonacci |
| D477,010 S | 7/2003 | Moritz et al. |
| 6,611,965 B1 | 9/2003 | Lee |
| 6,611,966 B1 | 9/2003 | Yamamoto et al. |
| 6,637,038 B1 | 10/2003 | Hussey |
| 6,641,263 B2 | 11/2003 | Olney |
| 6,665,885 B2 | 12/2003 | Masumoto |
| 6,691,324 B1 | 2/2004 | Nakamura |
| 6,704,944 B2 | 3/2004 | Kawanish et al. |
| 6,715,157 B2 | 4/2004 | Mage |
| 6,718,561 B2 | 4/2004 | Dondero |
| 6,728,974 B2 | 5/2004 | Wadsworth |
| 6,732,382 B2 | 5/2004 | Dondero |
| 6,732,383 B2 | 5/2004 | Cleary et al. |
| 6,772,448 B1 | 8/2004 | Hockaday et al. |
| 6,795,978 B2 | 9/2004 | Fournier et al. |
| 6,795,979 B2 | 9/2004 | Fournier |
| 6,832,389 B2 | 12/2004 | Simmons, Sr. |
| 6,859,946 B2 | 3/2005 | Fournier et al. |
| D503,736 S | 4/2005 | Cleary et al. |
| 6,896,366 B2 | 5/2005 | Rice et al. |

(56) References Cited

U.S. PATENT DOCUMENTS

| | | |
|---|---|---|
| D509,236 S | 9/2005 | Sheldon |
| 6,938,277 B2 | 9/2005 | Lindahl |
| 6,964,067 B1 | 11/2005 | Hartman |
| 6,986,169 B2 | 1/2006 | Nakamura |
| 7,039,959 B2 | 5/2006 | Dondero |
| 7,052,127 B2 | 5/2006 | Harrison |
| 7,058,992 B1 | 6/2006 | Ogonowsky |
| 7,062,797 B2 | 6/2006 | Khulusi |
| 7,073,208 B2 | 7/2006 | Penque, Jr. et al. |
| 7,096,514 B2 | 8/2006 | Khulusi |
| 7,100,215 B2 | 9/2006 | Shiue |
| 7,137,153 B2 | 11/2006 | Hussey |
| D537,098 S | 2/2007 | Sheldon et al. |
| 7,181,779 B2 | 2/2007 | Hussey |
| 7,192,137 B2 | 3/2007 | Ishibashi et al. |
| 7,200,875 B2 | 4/2007 | Dondero |
| D542,327 S | 5/2007 | Hsu |
| D542,829 S | 5/2007 | Hsu |
| D542,830 S | 5/2007 | Hsu |
| 7,260,850 B2 | 8/2007 | Ambuske et al. |
| 7,278,733 B2 * | 10/2007 | Olney .................... G02C 11/08 351/41 |
| 7,290,294 B2 | 11/2007 | Kita |
| D559,299 S | 1/2008 | Tabacchi |
| 7,343,631 B2 | 3/2008 | Lin |
| 7,356,854 B2 | 4/2008 | Sheldon |
| 7,370,374 B2 | 5/2008 | Penque et al. |
| 7,404,217 B2 | 7/2008 | Polinelli et al. |
| 7,510,279 B2 | 3/2009 | Van Atta et al. |
| D591,786 S | 5/2009 | Wang |
| 7,526,813 B2 | 5/2009 | Tominaga et al. |
| 2002/0029408 A1 | 3/2002 | Lindahl |
| 2002/0148034 A1 | 10/2002 | Lee |
| 2002/0157175 A1 | 10/2002 | Dondero |
| 2003/0093853 A1 * | 5/2003 | Maloney ................ A42B 3/185 2/425 |
| 2003/0209241 A1 | 11/2003 | Fournier et al. |
| 2003/0213050 A1 | 11/2003 | Fournier |
| 2003/0213051 A1 | 11/2003 | Fournier et al. |
| 2003/0217408 A1 | 11/2003 | Fournier |
| 2003/0217745 A1 | 11/2003 | Guay et al. |
| 2004/0000006 A1 | 1/2004 | Fournier et al. |
| 2004/0000308 A1 | 1/2004 | Fournier |
| 2004/0148674 A1 | 8/2004 | Simmons, Sr. |
| 2004/0226080 A1 | 11/2004 | Shiue |
| 2005/0018128 A1 | 1/2005 | Simmons, Sr. |
| 2005/0128426 A1 | 6/2005 | Shiue |
| 2005/0183191 A1 | 8/2005 | Tominaga et al. |
| 2006/0010585 A1 | 1/2006 | Chiang |
| 2006/0048289 A1 | 3/2006 | Shiue |
| 2006/0191062 A1 | 8/2006 | Matera |
| 2007/0033718 A1 | 2/2007 | Lin |
| 2008/0172778 A1 * | 7/2008 | Lysogorski ............ A42B 3/185 2/436 |
| 2009/0019620 A1 | 1/2009 | Reed |
| 2009/0038059 A1 | 2/2009 | McNeal et al. |
| 2011/0047681 A1 * | 3/2011 | Hedayat ................ A61F 9/025 2/435 |

FOREIGN PATENT DOCUMENTS

| | | |
|---|---|---|
| DE | 2943472 | 5/1981 |
| EP | 0504518 | 8/1991 |
| EP | 1095577 | 7/2000 |

* cited by examiner

GOGGLE FACIAL CUSHION

CROSS-REFERENCE TO RELATED APPLICATIONS

This application is a divisional patent application of U.S. patent application Ser. No. 13/233,740, filed on Sep. 15, 2011, the entire contents of which is expressly incorporated herein by reference.

STATEMENT RE: FEDERALLY SPONSORED RESEARCH/DEVELOPMENT

Not Applicable

BACKGROUND

The embodiment disclosed herein relates to a facial cushion for a goggle.

In various sports such as motocross, skiing, snowboarding, etc., the participant wears a goggle to prevent dirt, snow and other particulates from disturbing the wearer's eyes so that the wearer may focus on his/her surroundings. Unfortunately, in hot environments such as desert racing, the goggle provides another layer of insulation which may cause the wearer to sweat. The sweat may roll down the wearer's forehead and eventually drip into the wearer's eyes providing another nuisance which may distract the wearer from enjoying the sport, as well as prevent the wearer from performing at an optimal level. Sweat also increases moisture and may cause fogging on the goggle lens.

Additionally, these sports may also require the use of a helmet to protect the participant in the event of a fall. When a helmet is used, the straps of the goggle are strapped around the exterior of the helmet. The lens, frame and cushion are disposed immediately in front of the wearer's eyes. Unfortunately, the sides of the helmet have cushions and are offset away from the wearer's head. This causes the strap to pull outward and lift the left and right end portions of the cushion to gap away from the wearer's face. Dirt, snow and other particulates may enter the space between the goggle and irritate the wearer's eyes. Additionally, the air gap may increase wind circulation within the goggle and cause the wearer's eyes to become dry.

Accordingly, there is a need in the art for an improved goggle.

BRIEF SUMMARY

The embodiments disclosed herein address the needs discussed above, discussed below and those that are known in the art.

A cushion of a goggle may have an embossed pattern to reduce skin contact of the cushion on the wearer's face. Additionally, the embossed pattern increases the total surface area of a wicking material thereby increasing the rate at which sweat is removed from the wearer's face and evaporated. Moreover, since sweat rolling into the goggle is reduced or eliminated, undesired fogging of the lens of the goggle is also reduced or eliminated. The embossed pattern also creates an air space between the wearer's face and the cushion to facilitate cooling.

The cushion may be also have thicker left and right end portions compared to a middle portion so that the cushion maintains contact with the wearer's face even if the helmet 48 causes the goggle frame to open up when worn with a helmet.

More particularly, a facial cushion comprising a wicking material is disclosed. The facial cushion may define an interface surface. The interface surface may have a raised surface and a depressed surface. The raised surface may directly contact a wearer's face for wicking sweat away from the wearer's face. The depressed surface may be gapped away from the wearer's face when worn. This provides an air space between the wearer's face and the depressed surface.

The raised surface may be higher than the depressed surface about 0.25 mm to about 4.5 mm, and preferably between about 0.25 mm to about 2.5 mm. More particularly, the raised surface may be higher than the depressed surface about 1.5 mm.

The interface surface may have a plurality of raised surfaces and depressed surfaces which define a pattern of at least one parallelogram, triangle, square, rectangle, donut, circle, nested triangle, nested parallelogram, nested square, and combinations thereof. Any embossed design or pattern is contemplated regardless of whether the design or pattern repeats. The pattern may define one or more dead air spaces.

The raised surface may circumscribe an entire outer periphery of the facial cushion to provide a dead air space. Moreover, the depressed surface may circumscribe an entire inner periphery of the facial cushion.

The facial cushion may further comprise a foam padding wherein the foam padding may be attached to the wicking material.

In another embodiment, a goggle for use in conjunction with a helmet 48 is disclosed. The goggle may comprise a lens, a flexible frame, an elastic strap and a cushion. The lens may be disposed in front of eyes of a wearer. The flexible frame may be disposed in front of a face of the wearer and circumscribe the eyes of the wearer. The elastic strap may be disposed at opposed left and right end portions of the frame wherein the elastic strap is wrapped around the exterior of the helmet 48 and urges the goggle against the face of the wearer. The cushion may be disposed around a periphery of the flexible frame. Left and right end portions of the cushion may be thicker than a middle portion of the cushion so that the cushion maintains contact with the wearer's face when straps of the goggle are wrapped around an exterior of the helmet.

The left and right end portions of the cushion may be thicker compared to the middle portion by about 5 mm or more. The cushion's thickness may gradually increase from the middle portion to the left and right end portions.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Referring now to the drawings, a goggle 10 for use during motocross, snowing, skiing, and other sports and activities is shown. A facial cushion 24 of the goggle 10 may be fabricated from a series of layers 12, 28, 30 and 32 which provide comfort, cooling and moisture wicking functions to the wearer. The top layer 12 may provide the primary contact between the cushion and the wearer's face. The top layer may be fabricated from a wicking material to urge the sweat away from the wearer's face to prevent the sweat from entering the wearer's eyes. Moreover, the top layer 12 may be embossed with a pattern that defines a plurality of raised surfaces 14 and depressed surfaces 16. The depressed surfaces 16 do not contact the wearer's face when the goggle 10 is worn so as to form an air space between the top layer 12 of the cushion 24 and the wearer's face. The raised surfaces 14 contact the wearer's face when the goggle 10 is worn. Since the entire area of the top layer 12 does not contact the wearer's face, the total skin contact surface area between the cushion and the wearer's face is lower compared to prior art goggles. The reduction allows air to cool the wearer's face. Moreover, the surface area of the top layer 12 is increased since the surface area of the top layer 12 is the sum of the raised surfaces 14, depressed surfaces 16 and the sidewall surfaces 18. The increased total surface area of the top layer 12 increases moisture wicking and evaporation capabilities. Additionally, the increased moisture wicking and evaporation reduces or eliminates undesired fogging of the lens of the goggle.

Additionally, the facial cushion 24 may have a thicker middle portion 42 compared to the opposed distal end portions 44, 46. When the goggle 10 is worn over a helmet 48, the straps are wrapped around the exterior of the helmet 48. The helmet 48 being bulky pulls the opposed distal end portions of the cushion 24 apart. Fortunately, the left and right end portions 44, 46 are thicker at the left and right end portions 44, 46 so that the left and right end portions maintain contact with the wearer's face.

Figure 1:
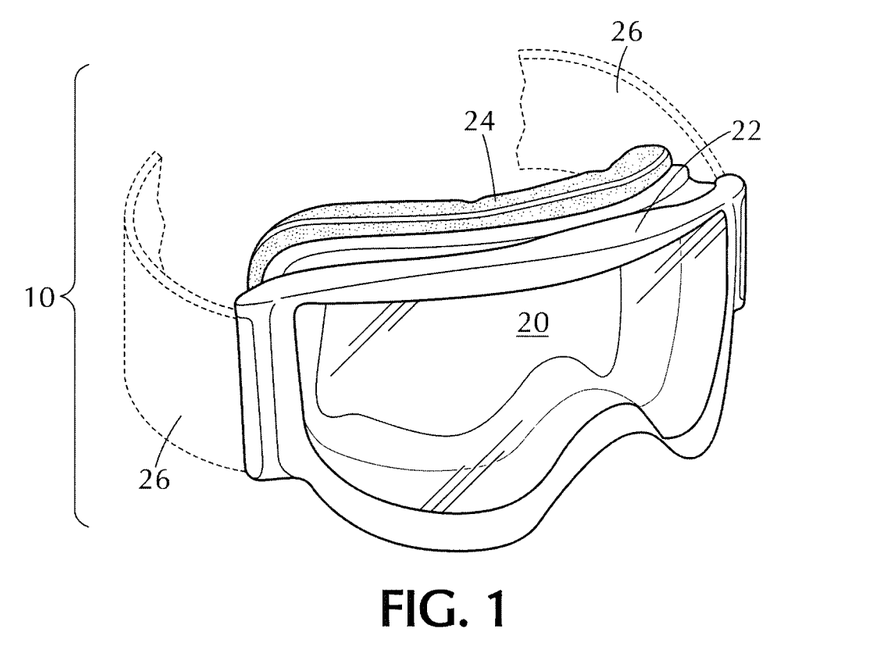
FIG. 1 is a perspective view of a goggle.

More particularly, referring now to FIG. 1, the goggle 10 may comprise a lens 20, a frame 22 and a facial cushion 24. The lens 20 may extend across both eyes of the wearer. However, it is also contemplated that the goggle may be a spectacle having two separate left and right lenses. The frame 22 may extend across the wearer's face and be positionable across the wearer's eyes. The frame 22 is shown as being a single frame for holding a single shield type lens 20 which extends across both eyes of the wearer. However, it is also contemplated that the frame 26 may be bifurcated and provide receptacles for left and right lens for protecting left and right eyes of the wearer. The single shield type lens 20 may also have a dual lens construction. The goggle 10 further comprises straps 26 that wrap around the wearer's head to press the lens 20, frame 22 and cushion 24 against the wearer's face and maintain the goggle 10 in place while the wearer participates in a physical sport. However, it is also contemplated that instead of straps 26, the goggle 10 may have left and right temples which seat onto the wearer's ears. The left and right temples may also have straps that go around the rear of the wearer's head to hold the goggle 10 on the wearer's face. Goggle as used herein refers to all types of eyewear whether a single lens such as that shown in the drawings, or bifurcated lens eyewear, face protection, eye protection, mask, etc.

Figure 2:
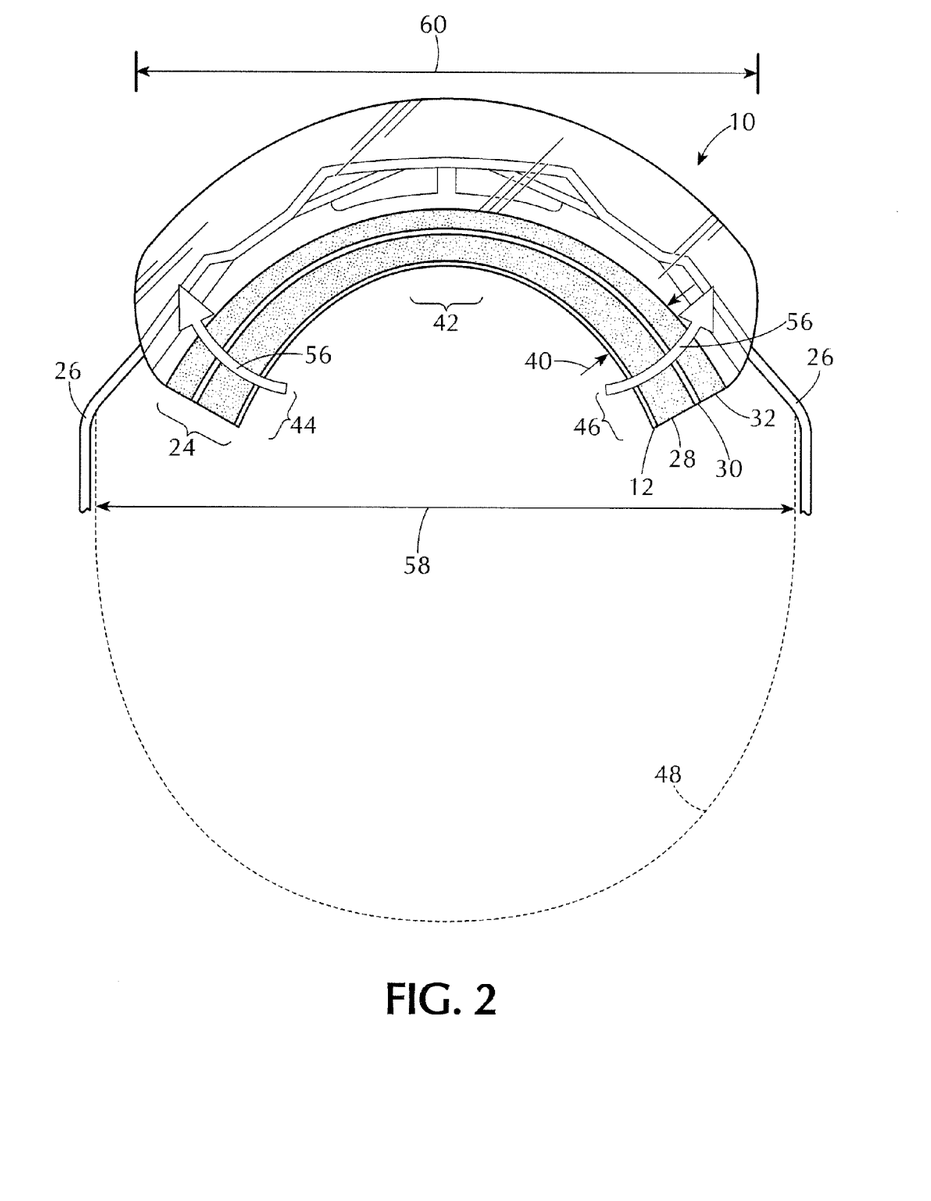
FIG. 2 is a top view of the goggle and a helmet, wherein left and right end portions of the facial cushion are thicker than the middle portion of the facial cushion.

The facial cushion 24 as shown in FIG. 2 may comprise a plurality of stacked layers 12, 28, 30 and 32. Each of the layers 12, 28, 30, 32 may provide one or more different functions. The layers 28, 30, 32 may facilitate shaping of the overall curved shape of the facial cushion 24 and also be compressible to accommodate any mismatch between the curvature of the wearer's face and the formed curvature of the facial cushion 24. One or more of the layers 28, 30, 32 may be rigid and approximate a curved configuration of a wearer's face. Although four layers 12, 28, 30, 32 are shown and described, it is contemplated that the facial cushion 24 may comprise the top layer 12 or the top layer 12 in addition to one or more layers which may serve cushioning and shaping functions.

Figure 3:
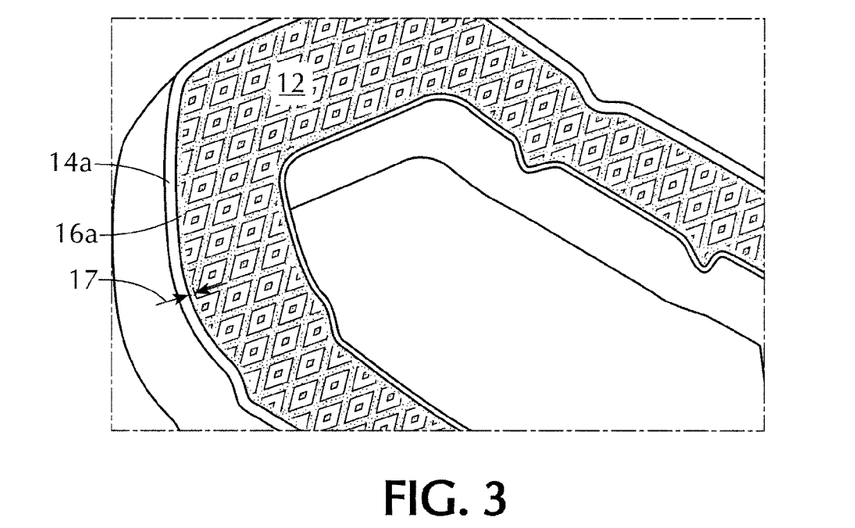
FIG. 3 is a rear perspective view of the goggle shown in FIG. 1 illustrating an embossed pattern on a facial cushion.

The top layer 12 provides the primary contact between the wearer's face and the goggle 10 facial cushion 24. During use, the straps 26 are wrapped around the person's head or over the helmet 48. The straps 26 being elastic and adjustable in length are cinched down so that the goggle is pressed against the wearer's face. Accordingly, the facial cushion 24 must provide comfort to the wearer. To increase comfort to the wearer, the top layer 12 may be fabricated from a wicking material which transfer sweat and liquid away from the wearer's face. The wicking material may have a high liquid absorption property. By way of example and not limitation, the wicking material may be fleece, polyester, microfiber fabrics, wool, silk, cotton, materials currently known in the art or developed in the future. The top layer 12 may be embossed with a reticulating geometric pattern as shown in FIG. 3 to increase wicking and provide cooling. By way of example and not limitation, the top layer 12 may be attached or adhered to the second layer 28. Other methods of attachment are also contemplated which are known in the art or developed in the future.

Figure 4:
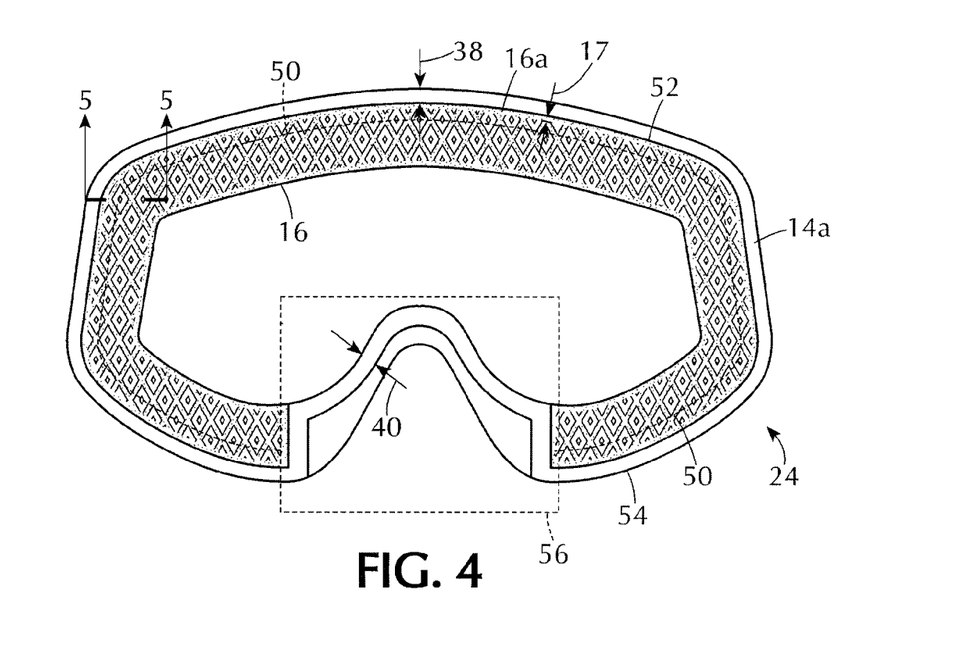
FIG. 4 is a rear planar view of the embossed pattern shown in FIG. 3.
Figure 5:
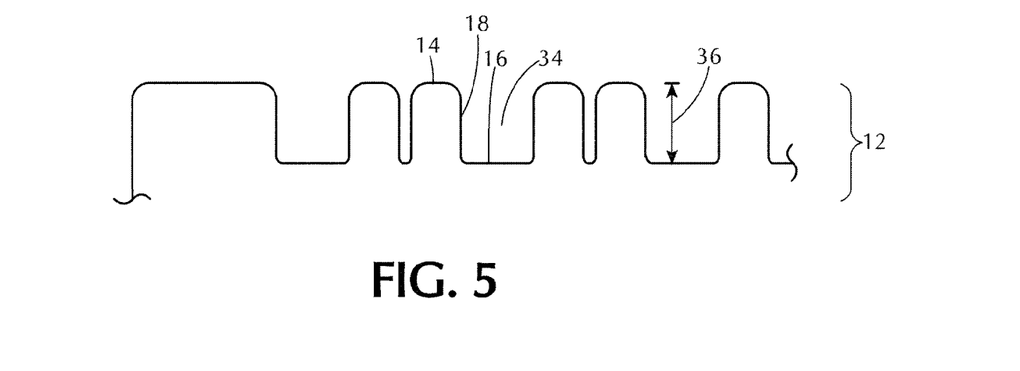
FIG. 5 is a cross sectional view of the embossed pattern shown in FIG. 4.

A planar view of the top layer 12 is shown in FIG. 4 which illustrates the configuration of the emboss made in the top layer 12. Referring now to FIG. 5, the embossed pattern may define a plurality of raised surfaces 14 and a plurality of depressed surfaces 16. These raised and depressed surfaces 14, 16 are joined to each other by sidewall surfaces 18. The raised surfaces 14 are offset from the depressed surfaces 16. In use, when the goggle 10 is worn, the raised surfaces 14 contact the wearer's face; whereas, the depressed surfaces 16 do not contact the wearer's face. An air space 34 is formed between the wearer's skin and the top layer 12, and more particularly, the depressed surface 16. The air space facilitates cooling. Also, the total skin contact area between the top layer 12 is less than the total skin contact area for a flat non-embossed top layer. By way of example and not limitation, the embossed pattern may provide for a reduction in total skin contact area about 35% between an embossed top layer and a flat, non embossed top layer. Other embossed patterns which provide for different % reductions are also contemplated.

The emboss pattern made in the top layer 12 also increases the total surface area of the top layer 12. The total surface area of the top layer 12 is equal to the sum of the surface areas of the raised surfaces 14, the depressed surfaces 16 and the sidewall surfaces 18. By increasing the surface area of the top layer 12, the top layer 12 is better able to wick and absorb sweat and water away from the wearer's face. Additionally, the added surface area also increases the rate of evaporation so that the cushion 24 does not retain as much liquid. By way of example and not limitation, the embossed pattern may provide for an increased surface area of the top layer 12 about 35% between an embossed top layer and a flat, non-embossed top layer 12. Other embossed patterns which provide for different % increases are also contemplated.

A distance 36 from the raised surface 14 to the depressed surface 16 may be between 0.25 mm and about 4.5 mm, and preferably, between about 0.25 mm and about 2.5 mm. More particularly, the distance 36 may be about 1.5 mm. The height of the raised surfaces 14 is shown as being at a consistent height. However, it is contemplated that the heights of the raised surfaces 14 may vary as desired. Additionally, the depth 36 of the depressed surfaces 16 below the raised surface 14 is shown in FIG. 5 as being consistent throughout the entire top layer 12. However, it is also contemplated that the depth 36 may vary at various areas of the top layer 12. The embossed pattern shown in FIG. 4 is shown as being a series of nested parallelograms with a central depressed surface 16 which is also configured as a parallelogram.

Figure 6:
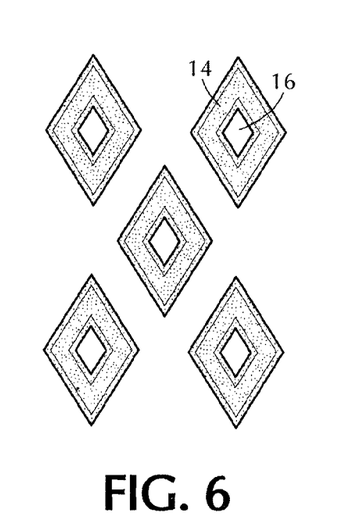
FIG. 6 is an enlarged view of the embossed pattern shown in FIGS. 3 and 4.
Figure 7:
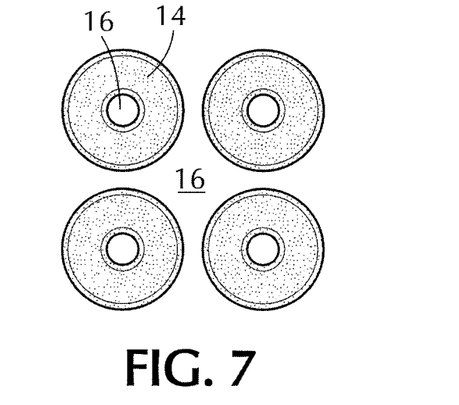
FIG. 7 is an alternate embossed pattern.
Figure 8:
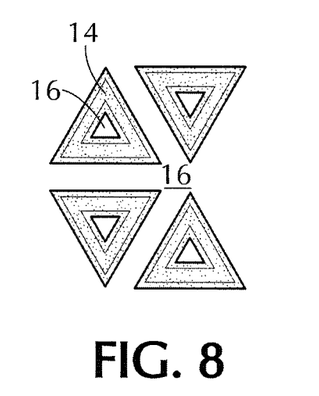
FIG. 8 is a further alternate embossed pattern.
Figure 9:
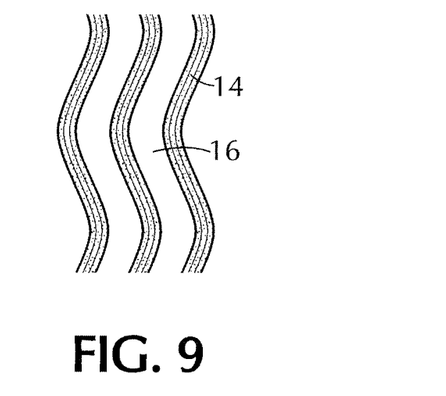
FIG. 9 is a further alternate embodiment of the embossed pattern.
Figure 10:
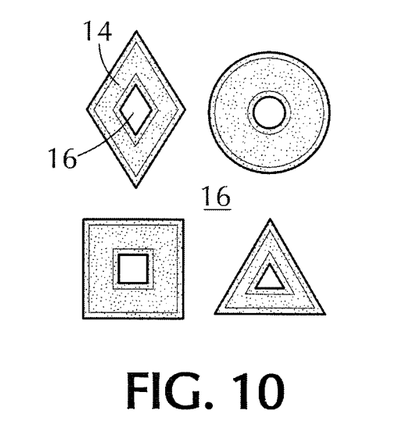
FIG. 10 is a further alternate embodiment of the embossed pattern.

Referring now to FIGS. 6-10, alternate embodiments of the embossed pattern are shown. In FIG. 6, the parallelogram pattern is shown. In FIG. 7, a donut pattern is shown. In FIG. 8, a nested triangular pattern in shown. In FIG. 9, a wavy pattern is shown. In FIG. 10, a combination of patterns shown in FIGS. 6, 7, 8 are shown as well as a rectangular pattern. The embossed pattern shown in the figures and described herein is for the purposes of illustration and not limitation. Accordingly, other embossed patterns are also contemplated for use in the facial cushion 24.

An outer periphery of the top layer 12 may have a single continuous raised surface 14a (see FIGS. 3 and 4) to seal the air within the goggle 10 and mitigate any particulate from inadvertently entering the space within the goggle 10. The single raised surface 14a is optional. The single raised surface 14a creates a dead air space between the depressed surface 16 and the wearer's face The raised surface 14a may be about 3 mm wide 38 around the outer periphery. At the nose area, the width 40 of the single raised surface 14a may be about 4.5 mm wide. Immediately adjacent the single raised surface 14a, there may be a depressed surface 16a (see FIG. 4). The depressed surface 16a adjacent to the single raised surface 14a may be about 1 mm wide 17 and extend around inner periphery of the single raised surface 14a except for a top portion of the nose area as shown in FIG. 4. The inner periphery of the top layer 12 may be formed with the depressed surface 16 except for the nose area, as shown in FIG. 4. However, it is also contemplated that the depressed surface 16 may be formed along the entire inner periphery. The single raised surface 14a may define a face seal for providing a dead air space between the depressed surface and the wearer's face. The facial cushion 24 may extend beyond an outer periphery 50 of the frame 22, as shown in FIG. 4. The outer periphery 54 of the top layer 12 may extend outside of the outer periphery 50 of the frame 22. Moreover, the inner periphery 52 of the single continuous raised surface 14a may extend outside of the outer periphery 50 of the frame 22 so that the single raised surface 14a is disposed outside of the outer periphery 50 of the frame 22. By way of example and not limitation, the outer periphery 54 of the top layer 12 may extend outside of the outer periphery of the frame 22 by about 6 mm.

The nose area 56 of the facial cushion 24 shown in FIG. 4 must traverse over and across the nose of the wearer. The single raised surface 14a traverses vertically so that the single raised surface 14a is now at the inner periphery of the top layer 12. The single raised surface 14a extends upward and over the bridge of the nose of the wearer.

Referring back to FIG. 2, the plurality of stacked layers 12, 28, 30 and 32 may collectively define a thickness 40 of the cushion 24. A thickness 40 of the facial cushion 24 at a middle portion 42 may be less compared to a thickness 40 of the left and right end portions 44, 46. The difference in thickness may be gradual, accelerated or stepped. Preferably, the facial cushion 24 gradually increases in thickness from the middle portion 42 toward the outer left and right end portions 44, 46. The difference in thickness may be attributed to a difference in thickness in any one or combination of the layers 12, 28, 30 and 32. When the goggle 10 is worn in conjunction with a helmet 48, the helmet 48 pulls the straps 26 outward. As shown in FIG. 2, a width 58 of the helmet 48 is generally wider than a width 60 of the goggle's frame. The wide helmet 48 pulls the left and right straps 26 outward and the ends of the goggle frame 22 outward as shown by arrows 56. This also pulls the left and right end portions 44, 46 of the facial cushion 24 outward and causes the left and right end portions 44, 46 of the facial cushion to lift off of the wearer's face in prior art goggles. In the embodiment shown in FIG. 2, the thicker cushion 24 at the left and right end portions 44, 46 accommodates the spreading open of the frame 22 so that the left and right end portions 44, 46 maintain constant contact with the wearer's face despite such pulling open of the goggle frame 22 by the straps 26 and the helmet 48. Air is not allowed to flow under the cushion 24 into the goggle 10 when worn with the helmet 48. Accordingly, this provides for an ergonomic fit.

For purposes of illustration and limitation, the total thickness of the cushion 24 at the opposed distal end portions 44, 46 of the cushion 24 may be about 19 mm. The fourth layer 32 may be about 6.5 mm thick. The third layer 30 may be about 2 mm thick. The second layer 28 may be about 10.5 mm thick. One or more of the layers 28, 30, 32 may decrease in thickness toward the middle portion 42 so that the total thickness of the cushion at the middle portion is about 14 mm. Although a 5 thickness mm difference between the middle portion 42 and the distal end portions 44, 46 is illustrated, it is also contemplated that the thickness difference may be greater than about 5 mm or less than 5 mm.

The stack of layers 12, 28, 30, 32 may serve different functions. By way of example and not limitation, the second, third and fourth layers 28, 30, 32 may be fabricated from various materials to provide cushion and shape to the facial cushion to provide comfort to the wearer.

The flexibility of the goggle 10 may be adjusted by increasing the thicknesses of the second and third layers 28, 30 while decreasing the thickness of the fourth layer 32. Conversely, the comfort of the goggle 10 may be enhanced by increasing the foam cushion layer 32. It is also contemplated that the soft foam cushion which is the fourth layer 32 may be disposed immediately adjacent to the top layer 12. In other words, the top layer 12 may be mounted to a foam cushion instead of the stiff second layer 28.

The thickness 40 of the cushion 24 may also vary vertically. By way of example and not limitation, the lower side of the cushion 24 near the mouth of the wearer may be thicker compared to the upper side of the cushion 24 near the forehead of the wearer. Conversely, the upper side of the cushion 24 may be thicker compared to the lower side of the cushion 24. Furthermore, it is also contemplated that the cushion 24 may have a constant vertical cross sectional thickness.

The above description is given by way of example, and not limitation. Given the above disclosure, one skilled in the art could devise variations that are within the scope and spirit of the invention disclosed herein, including various ways of forming the stack of layers 12, 28, 30, 32. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A goggle for use in conjunction with a helmet, the goggle comprising:
    a lens disposable in front of eyes of a wearer;
    a flexible frame engageable with the lens and disposable over a face of the wearer, the flexible frame circumscribing an eye of the wearer;
    an elastic strap disposed at opposed left and right end portions of the frame wherein the elastic strap is extendable around an exterior of the helmet and urges the goggle against the face of the wearer; and
    a cushion disposed around a periphery of the flexible frame and including a plurality of stacked layers, left and right end portions of the cushion being thicker than a middle portion of the cushion so that the cushion maintains contact with the wearer's face when the elastic strap is extended around the exterior of the helmet.

2. The goggle of claim 1 wherein the left and right end portions of the cushion have a thickness of about 5 mm or more compared to the middle portion.

3. The goggle of claim 1 wherein the cushion's thickness gradually increases from the middle portion to the left and right end portions.

4. The goggle of claim 1 wherein the flexible frame circumscribes both eyes of the wearer.

5. The goggle of claim 1, wherein at least one of the plurality of stacked layers is of a variable thickness.

6. The goggle of claim 1, wherein the plurality of stacked layers includes a top layer engageable with the face of the wearer and a plurality of intermediate layers positioned between the top layer and the frame.

7. The goggle of claim 6, wherein at least one of the plurality of intermediate layers is of a variable thickness.

8. The goggle of claim 6, wherein the top layer is formed of a wicking material.

9. The goggle of claim 8, wherein the top layer includes a raised surface and a depressed surface, the raised surface being engageable with the face of the wearer for wicking sweat away from the wearer's face, the depressed surface being spaced from the raised surface.

10. The goggle of claim 6, wherein the top layer includes a raised surface and a depressed surface, the raised surface being engageable with the face of the wearer for wicking sweat away from the wearer's face, the depressed surface being spaced from the raised surface.

11. A goggle for use with a helmet having an exterior, the goggle comprising:
    a flexible frame disposable over a face of the wearer, the flexible frame having opposed end portions and a periphery;
    an elastic strap coupled to the opposed end portions of the flexible frame, the elastic strap being extendable over the exterior of the helmet to urge the flexible frame toward the face of the wearer; and
    a cushion extending at least partially around the periphery of the flexible frame, the cushion including a plurality of stacked layers, an inner surface facing the flexible frame and an outer surface facing away from the flexible frame, the cushion defining opposed lateral end portions and a middle portion, the cushion having a thickness defined by the inner surface and the outer surface, the thickness being greater at the opposed lateral end portions than at the middle portion so that the cushion maintains contact with the wearer's face when the elastic strap is extended around the exterior of the helmet.

12. The goggle of claim 11 wherein the thickness at the lateral end portions of the cushion is about 5 mm or more compared to the middle portion.

13. The goggle of claim 11 wherein the thickness gradually increases from the middle portion to the lateral end portions.

14. The goggle of claim 11 wherein the flexible frame circumscribes both eyes of the wearer.

15. The goggle of claim 11, wherein at least one of the plurality of stacked layers is of a variable thickness.

16. The goggle of claim 11, wherein the plurality of stacked layers includes a top layer engageable with the face of the wearer and a plurality of intermediate layers positioned between the top layer and the frame.

17. The goggle of claim 16, wherein at least one of the plurality of intermediate layers is of a variable thickness.

18. The goggle of claim 16, wherein the top layer is formed of a wicking material.

19. The goggle of claim 18, wherein the top layer includes a raised surface and a depressed surface, the raised surface being engageable with the face of the wearer for wicking sweat away from the wearer's face, the depressed surface being spaced from the raised surface.

20. The goggle of claim 16, wherein the top layer includes a raised surface and a depressed surface, the raised surface being engageable with the face of the wearer for wicking sweat away from the wearer's face, the depressed surface being spaced from the raised surface.

* * * * *